(12) United States Patent
Lindner et al.

(10) Patent No.: US 8,695,405 B2
(45) Date of Patent: Apr. 15, 2014

(54) BEARING, ARRANGEMENT FOR DETERMINING PROPERTIES OF A LUBRICANT IN A BEARING AND METHOD FOR DETERMINING PROPERTIES OF A LUBRICANT IN A BEARING

(75) Inventors: Gerhard Lindner, Coburg (DE);
Martin Schmitt, Oberthulba (DE);
Josefine Schlemmer, Coburg (DE);
Sandro Krempel, Sonneberg (DE);
Hendrik Faustmann, Coburg (DE);
Christoph Brueckner, Altenstein (DE)

(73) Assignee: Bestsens AG, Coburg (DE)

( * ) Notice: Subject to any disclaimer, the term of this patent is extended or adjusted under 35 U.S.C. 154(b) by 454 days.

(21) Appl. No.: 12/976,774

(22) Filed: Dec. 22, 2010

(65) Prior Publication Data

US 2012/0067111 A1 Mar. 22, 2012

(30) Foreign Application Priority Data

Sep. 17, 2010 (EP) ..................................... 10177499

(51) Int. Cl.
*G01N 33/26* (2006.01)
(52) U.S. Cl.
USPC ......................................................... 73/53.05
(58) Field of Classification Search
USPC .......................................... 73/10, 53.05, 593
See application file for complete search history.

(56) References Cited

U.S. PATENT DOCUMENTS

| | | | | |
|---|---|---|---|---|
| 3,952,566 | A | * | 4/1976 | Jacobson ........................... 73/10 |
| 5,117,146 | A | * | 5/1992 | Martin et al. ............. 310/313 R |
| 5,686,661 | A | * | 11/1997 | Singh et al. .................. 73/54.41 |
| 6,513,365 | B1 | * | 2/2003 | Bruetting et al. .............. 73/32 A |
| 2002/0062694 | A1 | * | 5/2002 | Ehrfeld et al. .................... 73/593 |
| 2004/0045356 | A1 | * | 3/2004 | Dwyer-Joyce et al. .......... 73/579 |
| 2005/0196090 | A1 | * | 9/2005 | Maeda et al. .................. 384/624 |
| 2006/0150737 | A1 | * | 7/2006 | Pecher ............................. 73/593 |
| 2007/0277612 | A1 | * | 12/2007 | Ehrfeld et al. .................... 73/593 |

FOREIGN PATENT DOCUMENTS

| | | |
|---|---|---|
| EP | 1 598 569 A1 | 11/2005 |
| EP | 1 731 893 A1 | 12/2006 |

OTHER PUBLICATIONS

Lindner et al., On-Line Surveillance of Lubricants in Bearings by Means of Surface Acoustic Waves, IEEE Transactions on Ultrasonics, Ferroelectrics, and Frequency Control, vol. 57, No. 1, Jan. 2010.
International Search Report dated Feb. 1, 2012 as received in application No. PCT/EP2011/066245.

(Continued)

*Primary Examiner* — Hezron E. Williams
*Assistant Examiner* — David Z Huang
(74) *Attorney, Agent, or Firm* — Maschoff Brennan

(57) ABSTRACT

A bearing including a first and a second bearing element that are movable relative to one another, a lubricant arranged between the first and the second bearing element for reducing the friction between the first and the second bearing element, at least one transmitter for exciting acoustic waves in the first or the second bearing element, the transmitter being arranged on the first or the second bearing element; at least one receiver for receiving acoustic waves evoked by the transmitter, the receiver being arranged on the first or the second bearing element, wherein information related to properties of the lubricant can be determined using a signal generated by the receiver upon receipt of acoustic waves evoked by the transmitter. The invention is also related to a method for determining properties of a lubricant in a bearing.

18 Claims, 9 Drawing Sheets

(56) References Cited

OTHER PUBLICATIONS

Written Opinion of the International Searching Authority dated Feb. 1, 2012 as received in application No. PCT/EP2011/066245.
Rayleigh Wave, Wikpedia, accessed on Jul. 2, 2013 http://en.wikipedia.org/wiki/Rayleigh_wave.
Lamb Waves, Wikpedia, accessed on Jul. 2, 2013 http://en.wikipedia.org/wiki/Lamb_waves.
Gerhard Lindner et al., On-line surveillance of lubricants in bearings by means of surface acoustic waves, Jan. 2010.
Gerhard Lindner et al., On-line surveillance of lubricants in bearings by means of surface acoustic waves, Institute of Sensor and Actuator Technology.

* cited by examiner

BEARING, ARRANGEMENT FOR DETERMINING PROPERTIES OF A LUBRICANT IN A BEARING AND METHOD FOR DETERMINING PROPERTIES OF A LUBRICANT IN A BEARING

The invention relates to a bearing according to claim 1, a bearing according to claim 15, an arrangement for determining properties of a lubricant in a bearing according to claim 15 and a method for determining properties of a lubricant of a bearing according to claim 18.

Bearings (for example, friction type or rolling element bearings) usually contain a lubricant (e.g. oil) for controlling the friction between the movable parts of the bearing. The monitoring of the properties (such as the quantity or the viscosity) of the lubricant in a bearing is important in order to be able to assure a reliable operation of the bearing. For example, optical and ultra sonic methods are known for lubricant monitoring.

It is an object of the invention to provide a possibility for monitoring properties of a lubricant in a bearing as reliable as possible.

According to the invention, a bearing is provided, comprising:
- a first and a second bearing element that are movable relative to one another;
- a lubricant arranged between the first and the second bearing element for reducing the friction between the first and the second bearing element;
- at least one transmitter for exciting acoustic waves in the first or the second bearing element, the transmitter being arranged on the first or the second bearing element;
- at least one receiver for receiving acoustic waves evoked by the transmitter, the receiver being arranged on the first or the second bearing element, wherein information related to properties of the lubricant can be determined using a signal generated by the receiver upon receipt of acoustic waves evoked by the transmitter.

In particular, the transmitter is configured to excite surface acoustic waves in the first or the second bearing element. Especially, concurrent acoustic waves in the form of Lamb or Lamb-Rayleigh waves are generated travelling from the transmitter to the receiver in the first or the second bearing element.

If a lubricant is present on a surface of the first or second bearing element at least a part of the acoustic waves propagating in the bearing element will be converted into acoustic waves in the lubricant provided that the acoustic waves excited in the first or second bearing element comprise displacements at the surface of the substrate that have a non-vanishing sagittal component (which is fulfilled by Lamb- or Rayleigh-Waves) and provided that the velocity of sound in the lubricant is smaller than the wave velocity in/on the first or second bearing element, which is true for common lubricants (e.g. oil) and common materials of bearing elements (e.g. metal). Further, the frequency of the waves must be chosen appropriately as will be discussed below.

Therefore, the presence of the lubricant (e.g. a lubricant film) on a surface of the bearing element in which acoustic waves are excited will cause a change of the acoustic waves arriving at the receiver and thus a change of the (electrical) signal generated by the receiver upon receipt of the waves. For example, the amplitude of the receiver signal will decrease depending on the amount of lubricant (e.g. the thickness of a lubricant film) present on an inner surface of the bearing element. Also, variations of other properties of the lubricant (such as its temperature or composition) will result in a change of the receiver signal. Thus, by detecting and evaluating the acoustic waves travelling in the first or second bearing element information about some important lubricant properties can be derived.

According to an embodiment of the invention, the transmitter is arranged at (on or in) the first bearing element and the receiver is arranged at the second bearing element. Especially, the transmitter is arranged on a surface of the first bearing element and the second bearing element is arranged on a surface of the second bearing element. However, e.g. depending on the type of the bearing, the transmitter and the receiver can also be arranged at the same bearing element, i.e. both the transmitter and the receiver are arranged either on the first or the second bearing element.

In order to excite surface acoustic waves in the form of Lamb waves, Lamb-Rayleigh or Rayleigh waves, the frequency of the excited waves in the bearing element is adapted to the thickness of the bearing element such that concurrent surface acoustic waves are excited that propagate on both a first side and a second (opposite) side of the bearing element, wherein the first side is an inner side being in contact with the lubricant and the second side is an outer side of bearing element.

In the case of Lamb waves or Lamb-Rayleigh-waves the displacement of opposite surfaces of the bearing element excited by the transmitter is correlated such that, in particular, the amplitude and/or the phases of the displacement movement of the inner and outer surfaces of the bearing element are interrelated. For example, the acoustic waves excited in the bearing element will be mainly or only of the Lamb wave type if the thickness of the bearing is substantially smaller (e.g. at least five times smaller) than the wavelength of the excited acoustic waves. The frequency of the excited acoustic waves thus has to be chosen depending on the thickness of the bearing element and taking into account the dispersion relation of the Lamb waves.

However, as set forth above, e.g. also a transition type of Lamb waves and Rayleigh waves can be used, i.e. the thickness (the distance between the outer and the inner side) of the bearing element can be of the same order of magnitude as the wavelength of the excited acoustic waves. In that case, there can still be a correlation between the displacement movement of the opposite surfaces of the bearing element. For example, the thickness of the bearing element is in the range between 0.1 mm to 5 mm. The excitation frequency may be chosen to be in the range between 500 kHz and 2 MHz, in particular between 800 kHz and 1.5 MHz.

The transmitter and/or the receiver may be interdigital piezo-electric transducers. It is noted, however, that the term "transmitter" is not restricted to a piezo-electric transducer. Other embodiments of the invention comprise a transmitter in the form of a (e.g. pulsed) laser that excites the acoustic waves in the substrate based on thermoelastic effects. Also, a wedge ("wedge converter") could be used to excite the acoustic waves or a comb-like vibrator ("comb converter"), wherein the wedge converter and/or the comb converter may be used in combination with a piezo-electric transducer. Of course, different transmitter types could also be used in combination. Also, the receiver does not necessarily have to be an interdigital piezo-electric transducer either. For example, a receiver in the form of an optical displacement detector such as an interferometer or a laser-doppler-vibrometer could be used.

For example, the bearing is a friction type bearing such that a surface of the first bearing element can slide over a surface of the second bearing element, wherein the friction between the two surfaces is reduced by the lubricant. The first and/or the second bearing element can be connected to further parts.

In another embodiment, the bearing is a rolling element, wherein that at least one rolling element is arranged between the first and the second bearing element. For example, the rolling element is a ball (ball bearing) or a cylinder (roller bearing).

In particular, both the transmitter and the receiver are arranged on an outer side, i.e. on a side of the first or the second element that faces away from the rolling element. For example, the rolling element bearing is an axial bearing, the first bearing element forming an outer ring and the second bearing element forming an inner ring of the bearing. The inner ring, for example, is configured to receive a shaft. It is, however, also conceivable that the second bearing element itself is a machine part (e.g. a shaft) that is mounted on the first bearing element. Thus, it is possible to determine properties of the lubricant only by arranging the transmitter and the receiver on an outer surface of the bearing without having to arrange a sensor within the bearing interior. It is noted that, of course, the invention could also be used with a linear rolling element bearing.

According to another variant of the invention, the transmitter and the receiver are arranged on an outer surface of the outer ring of the bearing. In particular, the transmitter is arranged and configured in such a way that first acoustic waves are excited travelling along the outer ring in clockwise direction and second acoustic waves travelling along the outer ring in anti-clockwise direction.

For example, the receiver is arranged and configured in such a way that the path length between the transmitter and the receiver in clockwise direction is different from the path length between the transmitter and the receiver in anti-clockwise direction. In this way, a single transmission signal creates two easily distinguishable signals at the receiver. These two signals equally depend on external parameters (such as, for example, the temperature of the surroundings of the bearing) but correspond to different paths length of the interaction between the acoustic waves and the lubricant and/or the rolling elements of the bearing. Therefore, using the difference of these two signals, it is possible to eliminate the influence of external parameters. It is noted that also for a linear bearing this principle could be used, for example by using two receivers that are positioned at different distances from the transmitter.

The bearing may also comprise evaluating means configured for determining information related to properties of the lubricant using a signal generated by the receiver upon receipt of acoustic waves evoked by the transmitter. In particular, the evaluation means are configured to evaluate a first signal generated by the receiver evoked by the first acoustic waves and a second signal generated by the receiver evoked by the second acoustic waves and to use a difference between the first and the second signal for determining the information related to properties of the lubricant.

Evaluating the receiver signal can comprise evaluating the amplitude and the time response (transmission time) of the signal. As set forth above, the presence of a lubricant on a bearing surface will cause some of the acoustic wave energy in the bearing element to be converted into wave energy in the lubricant such that the amplitude of the acoustic wave arriving at the receiver will be smaller if a lubricant is present compared to a bearing without lubricant.

As to evaluating the transmission time of the receiver signal, the transmitter, for example, excites pulsed acoustic waves in the bearing element which have a certain propagation time (the "transmission time") from the transmitter to the receiver (depending on the path they take between the transmitter and the receiver). Modifications of the interface between the inner surface of the bearing element and the interior of the bearing will influence the transmission time (i.e. the time a wave front or an acoustic pulse needs to run from the transmitter to the receiver) of the acoustic waves in the bearing. Thus, evaluating changes of the transmission time may contribute to the determination of properties of a lubricant in the bearing.

The evaluation means may be realised as a programmed electronic circuit or a software running on a programmable device.

According to another aspect of the invention, a bearing, in particular as described above, is provided, comprising:
  a first and a second bearing element that are movable relative to one another;
  a lubricant arranged between the first and the second bearing element for reducing the friction between the first and the second bearing element;
  means for exciting acoustic waves in the first or the second bearing element;
  means for receiving acoustic waves evoked in the first or the second bearing element, wherein information related to properties of the lubricant can be determined using a signal generated by the means for receiving acoustic upon receipt of acoustic waves, wherein
  the means for exciting the acoustic waves and the means for receiving the acoustic waves are configured in such a way that first acoustic waves travelling along a first path before being received by the receiving means and second acoustic waves travelling along a second path before being received by the receiving means, wherein the path lengths of the first and the second paths are different.

For example, the means for exciting acoustic waves in the first or the second bearing element comprise at least one transmitter and the means for receiving acoustic waves comprise at least on receiver, wherein possible configuration of the transmitter, the receiver and the bearing elements have been discussed above. For example, at least one of the bearing elements is ring shaped and both the transmitter and the receiver are arranged at this ring shaped bearing element. It is also conceivable that the receiving means comprise two receivers wherein the different path lengths are realized by the distance between the transmitter and the first and the second receiver, respectively.

The invention also relates to an arrangement for determining properties of a lubricant of a bearing having a first and a second bearing element, comprising:
  at least one transmitter for exciting acoustic waves in the first and/or the second bearing element;
  at least one receiver for receiving acoustic waves evoked by the transmitter, wherein properties of the lubricant can be determined using a signal generated by the receiver upon receipt of acoustic waves evoked by the transmitter;
  attachment means for attaching the transmitter and the receiver to the first or second bearing element.

The attachment means may allow a detachable connection of the transmitter and/or receiver to the bearing elements. For example, the attachment means comprise latching elements. In particular, the attachment means allow the transmitter and/or receiver to be arranged in a way as described above.

The arrangement according to the invention may further comprise evaluating means configured for determining information related to properties of the lubricant using a signal generated by the receiver upon receipt of acoustic waves evoked by the transmitter. In particular, the evaluating means are configured as set forth above.

The invention also comprises a method for determining properties of a lubricant of a bearing, the method comprising the steps of:
  a) providing a bearing having a first and a second bearing element that are movable relative to one another;
  b) arranging at least one transmitter at the first or the second bearing element and exciting acoustic waves in the first and/or the second bearing element by the use of a transmitter;
  c) arranging at least one receiver and receiving acoustic waves evoked by the transmitter using the receiver;
  d) determining information related to properties of the lubricant by evaluating a signal generated by the receiver upon receipt of acoustic waves evoked by the transmitter.

For example, a reference value of the signal amplitude is determined for the bearing without the lubricant and evaluating the signal comprises determining the difference between the reference value and the amplitude of the received signal. A signal (alarm signal) may be generated if the difference drops below a predetermined value. Also, it is possible that a calibration is carried out. For example, amplitude values are determined for a plurality of different lubricant quantities (i.e. bearing fillings) as explained in more detail below.

Determining information related to properties can comprise determining a thickness of a lubricant layer on a surface of the first and/or the second bearing element. In particular, a calibration is carried out in order to be able to determine absolute values of the thickness.

Also, the bearing can be a rolling element bearing (as describe above) such that a periodic receiver signal is generated when the bearing is operated, wherein the method comprises the steps of:
  registering the periodic receiver signal by the receiver;
  evaluating the periodic receiver signal by determining an average amplitude and/or an average transmission time of the signal; and
  determining the amount of lubricant present in the bearing using the determined average amplitude and/or an average transmission time of the signal.

Thus, in particular after a suited calibration of the bearing, the amount of lubricant in the bearing can be determined using the receiver signal. It is also possible to use minimum amplitude or transmission time values in addition or instead of the average amplitude or transmission time. Further, the average of the periodic changes of the amplitude or the transmission time could be used.

The possible arrangement and operation of the transmitter and the receiver has been described above.

The embodiments of the invention will be described in more detail hereinafter with reference to the drawings, in which.

Figure 1:
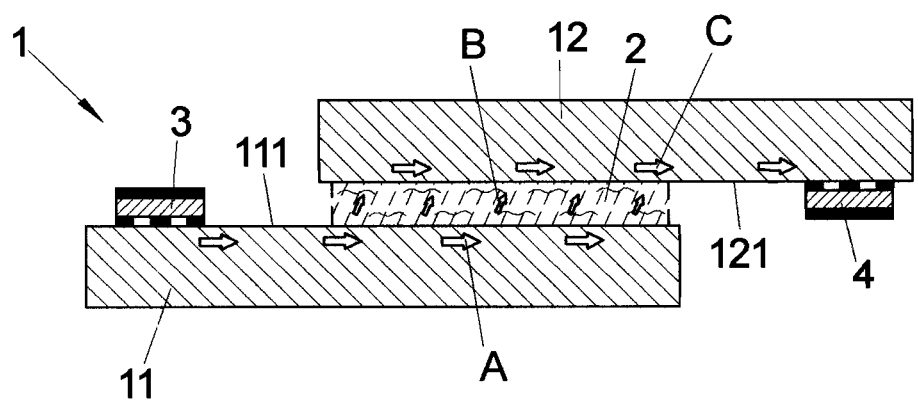
FIG. 1 illustrates a bearing according to a first embodiment of the invention.

FIG. 1 shows a bearing 1 in the form of a friction type bearing (plane bearing), which comprises a first bearing element in the form of a cuboid body 11 and a second cuboid body 12. The two bodies 11, 12 can be moved relative to one another, wherein a surface 111 of the first body 11 can slide over a surface 121 of the second body 12. The surfaces face each other and extend essentially parallel. The first and/or the second body can be connected to further parts (not shown) which shall be moved relative to one another.

Between the surfaces 111, 121 a lubricant 2 is arranged for reducing the friction between the two bodies 11, 12 (i.e. between the surfaces 111, 121 of the bodies). In order to be able to determine some of the properties of the lubricant surface acoustic waves A are excited on the first body 11. For this, a transmitter 3 is arranged on the surface 111 of the first body 11, wherein the transmitter 3 is positioned outside the overlapping region between the first and the second body 11, 12 (i.e. in a distance to the lubricant 2). Further, a receiver 4 is arranged on the surface 121 of the second body 12.

The acoustic waves A initially travel along the first body 11. However, in the region of lubricant 2 at least a part of the acoustic waves A are converted into sound waves B in the lubricant 2 due to mode convertion effects described above. The converted waves propagate in the lubricant towards the second body 12 where a part of the waves is reconverted into surface acoustic waves in the second body 12. These reconverted waves C travel along the second body 12 towards the receiver 4 where they are detected and an electrical signal is generated upon detection.

The properties of the electrical signal generated by the receiver 4 depend on the properties (amplitude, transmission time) of the acoustic waves C, which in turn depend on the mode convertion effect and thus on the properties of the lubricant 2 (for example, the volume of the lubricant present in the bearing). Therefore, evaluating the amplitude and time behaviour of the electrical signal generated by the receiver 4 allows the determination of information about the properties of the lubricant. Examples of receiver signals are shown in FIGS. 2A and 2B.

Figure 2:
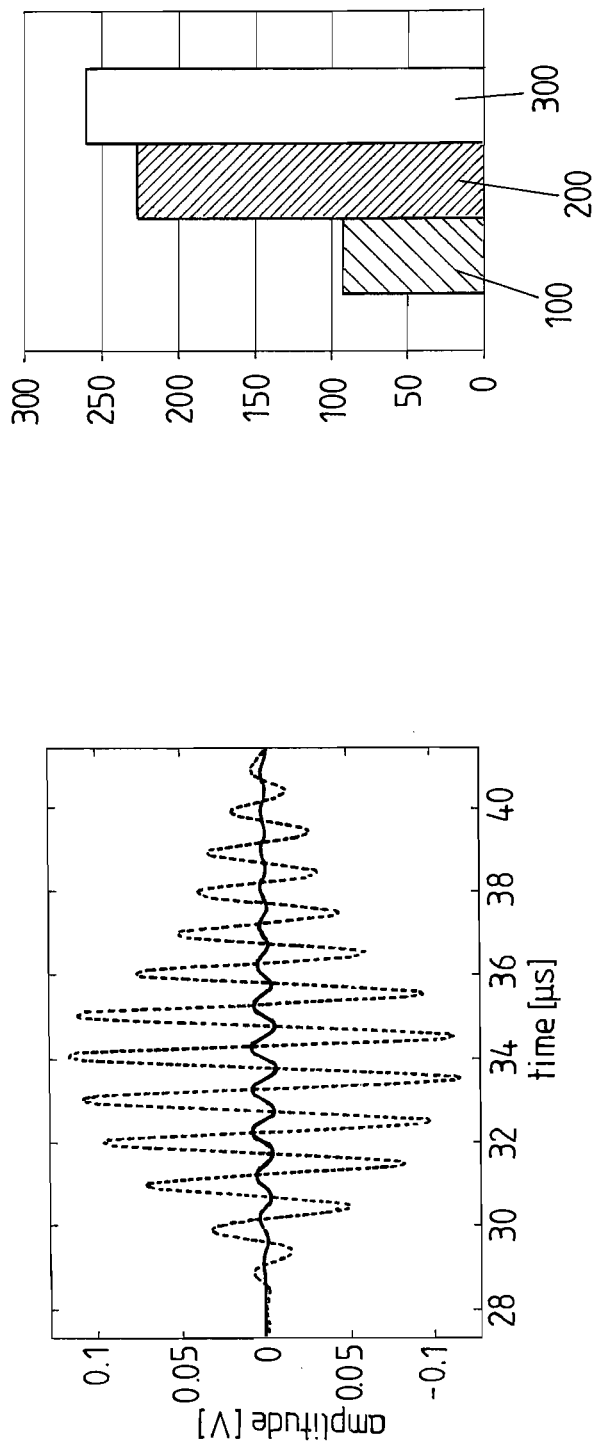
FIG. 2A illustrates a receiver signal obtained with the bearing arrangement of FIG. 1.
FIG. 2B illustrates receiver signal amplitudes for different lubricant situations with respect to the bearing arrangement of FIG. 1.

FIG. 2A shows the receiver signal obtained in the friction bearing arrangement according to FIG. 1. The amplitude of the signal drastically increases if a lubricant is present in the bearing (continuous line: bearing without lubricant, dashed line: with lubricant). This is due to the fact that a part of the acoustic waves in lower bearing body 1 couples via the lubricant 2 into the upper bearing body 2 such that it will be received by the receiver 4. FIG. 2B illustrates the maximum amplitude of the receiver signal for the case that no lubricant is present (bar 100), oil is used as the lubricant (bar 200) and grease is used as lubricant (bar 300).

Figure 3:
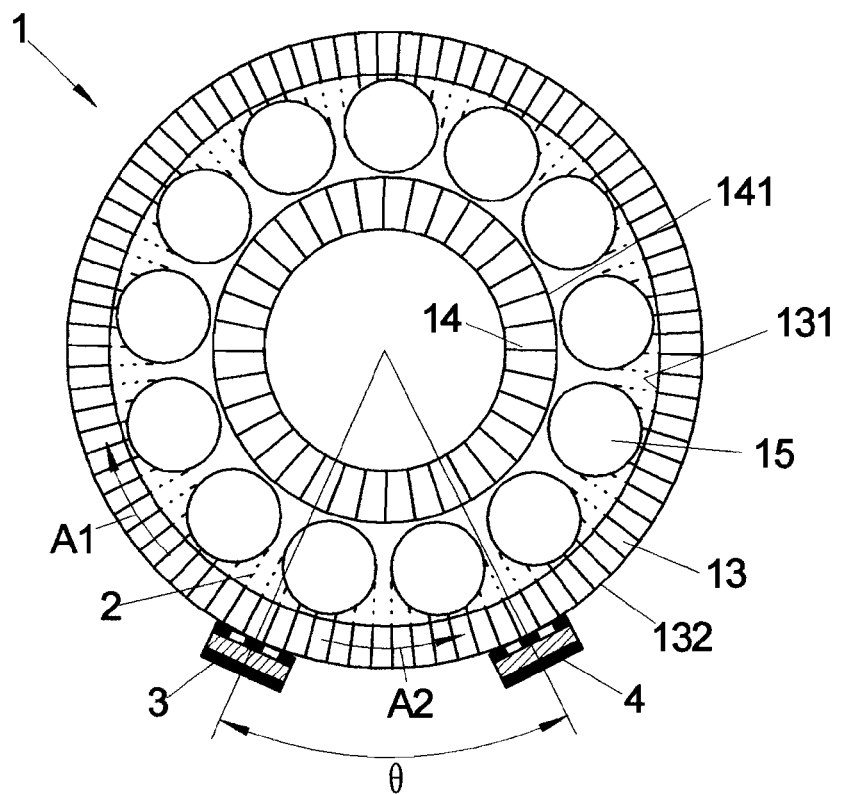
FIG. 3 shows a top view of a bearing according to a second embodiment of the invention.
Figure 4:
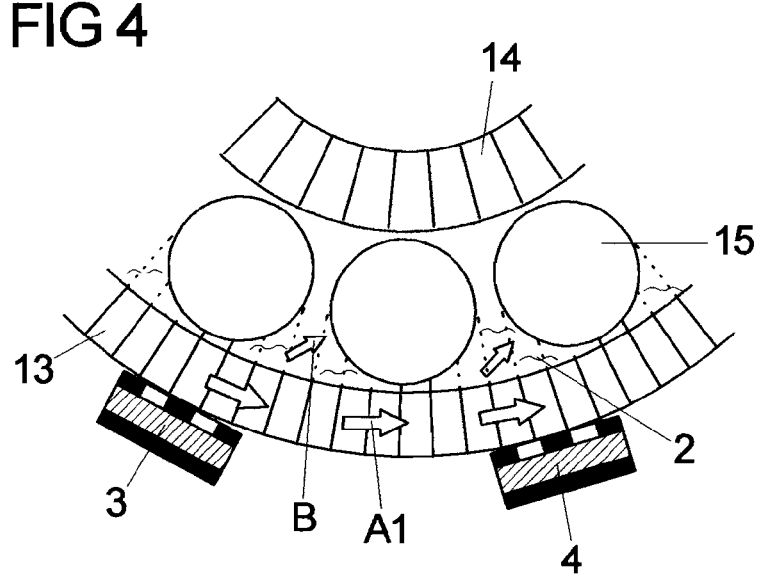
FIG. 4 shows an enlarged detail of FIG. 2.

FIG. 3 (top view) and FIG. 4 (side view) relate to another embodiment of the invention, wherein the bearing 1 is a rolling element bearing in the form of a ball bearing.

The bearing 1 comprises a first bearing element in the form of an outer ring 13 and a second bearing element in the form of an inner ring 14 having a smaller diameter than the outer ring and being positioned within the outer ring. Between an inner surface 131 of the outer ring and an outer surface 141 (facing towards surface 131) of the inner ring 14 a plurality of rolling elements in the form of spheres 15 are arranged. Additionally, at least a part of the volume between the inner surface 131 and the surface 141 is filled with a lubricant 2.

In order to measure properties (e.g. the filling level) of the lubricant 2 an acoustic sensor arrangement is provided, the sensor arrangement comprising means for exciting acoustic waves in the bearing elements in the form of a transmitter 3 and means for receiving the acoustic waves in the form of a receiver 4. Both the transmitter 3 and the receiver 4 are arranged on an outer surface 132 of the outer ring 13, the outer surface facing away from the inner surface 131.

The transmitter 3 excites surface acoustic waves in the outer ring 13 which are detected by the receiver 4, wherein the amplitude and the time response of the receiver signal depend on the properties of the interface between the inner surface 131 of the outer ring 13 and its surroundings. In particular, the receiver signal depends on the presence and the properties of the lubricant as is it in contact with the inner surface 131 such that mode convertion of the surface acoustic waves generated in the outer ring will occur as set forth above and as illustrated in FIG. 4. A part of the acoustic waves in the outer ring 13 is coupled into the lubricant 2 (arrows B) such that for example the amplitude of the receiver signal will drop depending, for example, on the amount of lubricant present between the rings 13 and 14.

The transmitter 3 is structured and arranged in such a way that first acoustic waves A1 that travel along the outer ring 13 in clockwise direction (with respect to the top view of the bearing) and second acoustic waves A2 are generated that travel along the outer ring 13 in anti-clockwise direction. Further, the transmitter 3 is arranged relative to the receiver 4 in such way that the path length between the transmitter and the receiver in clockwise direction is longer than the path length between the transmitter and the receiver in anti-clockwise direction. Thus, two well distinguishable signals will be generated by the receiver upon receipt of the first and the second acoustic waves, wherein external distortions could be eliminated or at least reduced by using a differential signal, i.e. by subtracting the signal corresponding to the second acoustic waves from the signal corresponding to the first acoustic waves or vice versa.

For example, the transmitter and the receiver are separated by an angle θ of 30°. Of course, other angles are possible.

Figure 5A:
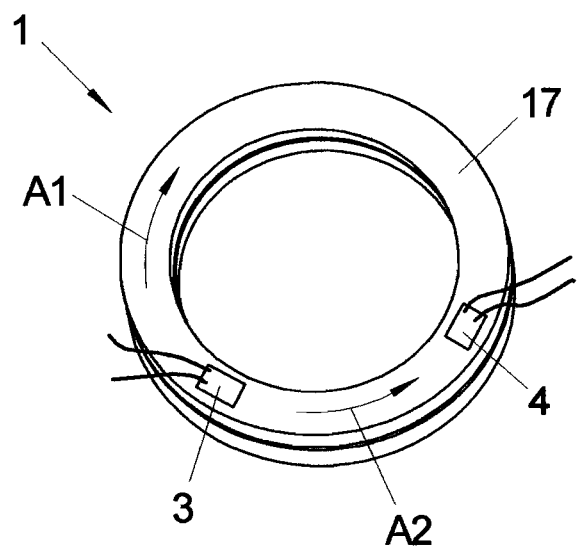
FIG. 5A shows a top view of a bearing according to a third embodiment of the invention.
Figure 5B:
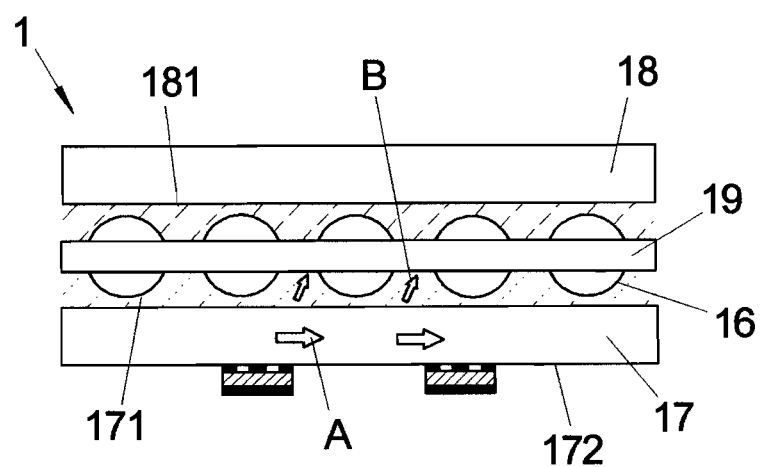
FIG. 5B shows a side view of the arrangement of FIGS. 5A and 5B.

FIGS. 5A (top view) and 5B (side view) are related to another embodiment of the invention, wherein the bearing is a rolling element bearing in the form of a cylinder roller bearing. This bearing comprises a plurality of rolling elements in the form of cylinders 16 arranged between a first bearing element in the form of a first ring 17 and a second bearing element in the form of a second ring 18, wherein the diameter of the first ring compares to the diameter of the second ring. Further, a cage 19 is provided for holding the cylinders 16. The axis of the cylinders 16 is orientated radially with respect to the rings 17, 18 such that the cylinders will roll between an inner surface 171 of the first ring and an inner surface 181 of the second ring 18, the surfaces 171 and 181 facing one another. Further, a lubricant 2 is present between the first and the second ring 17, 18.

A transmitter 3 and a receiver 4 are arranged on an outer side 172 of the first ring 17. Surface acoustic waves A are generated and detected using the transmitter 3 and the receiver 4 as set forth with respect to the other embodiments such that properties of the lubricant 2 can be detected even when the bearing 1 is in operation. In particular, the transmitter 3 and the receiver 4 are arranged similarly to FIG. 3 such that first and second acoustic waves A1, A2 are generated in the first ring 17 travelling in opposite directions and having different path lengths from the transmitter to the receiver. It is noted that of course more than one transmitter and/or more than one receiver could be used. For example, another receiver could be arranged on the first ring or on the second ring.

Figure 6:
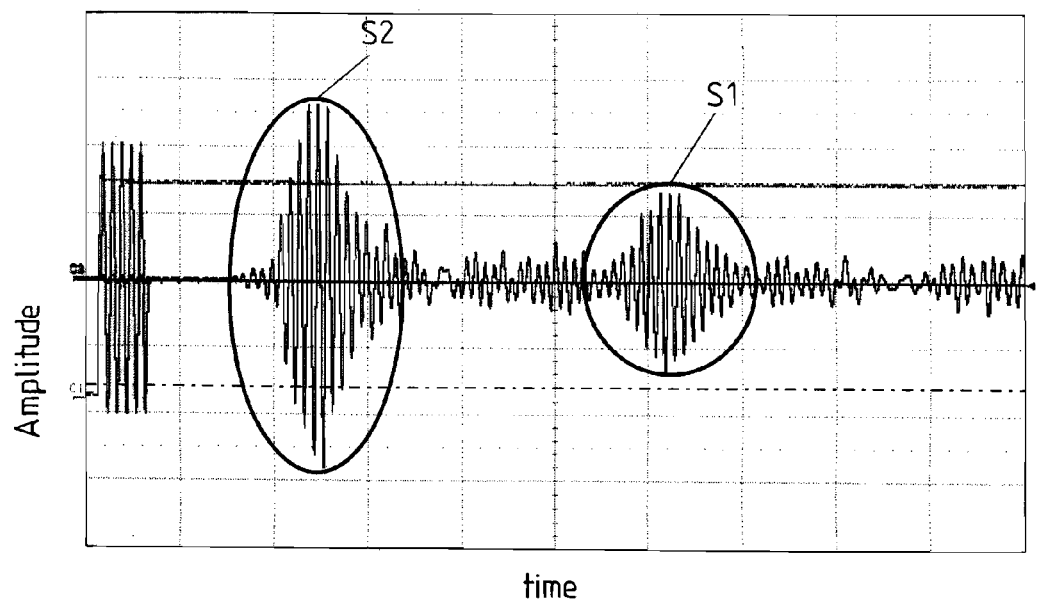
FIG. 6 illustrates a receiver signal generated using the arrangement of FIGS. 5A and 5B.

Because of this arrangement of the transmitter and the receiver two discernable signals will appear in the receiver signal as shown in FIG. 6. The first signal (pulse) S2 corresponds to the second acoustic waves A2 travelling along the shorter path between the transmitter 3 and the receiver 4, wherein the later signal S1 corresponds to the first acoustic waves A1 propagating along the longer path.

Figure 7A:
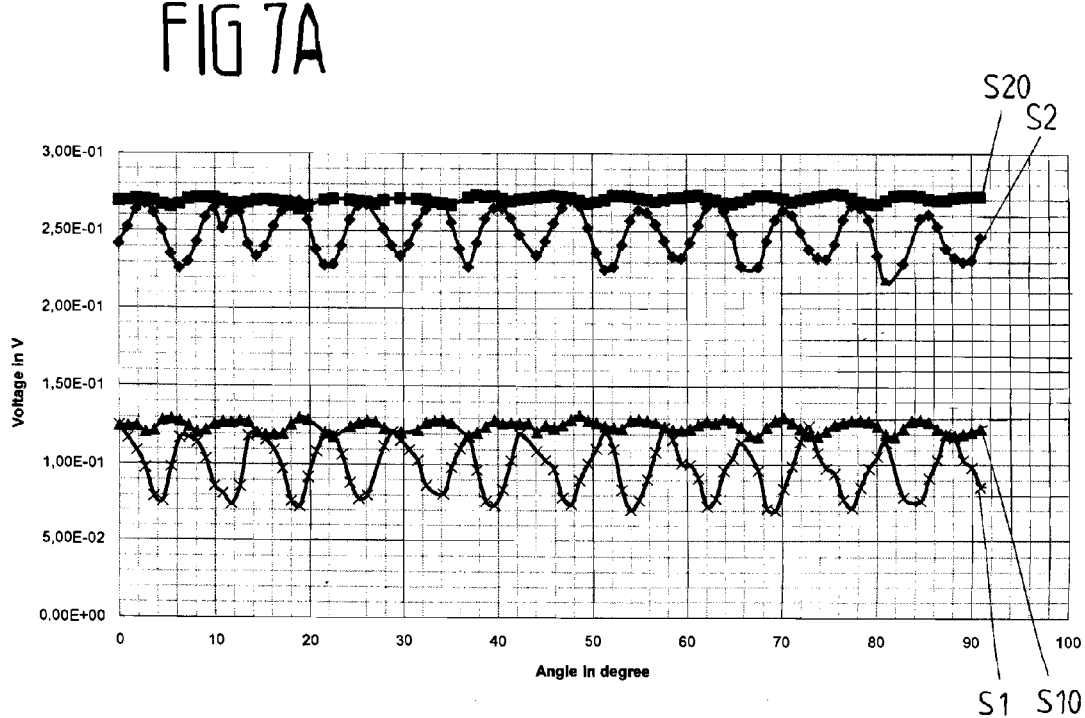
FIGS. 7A, 7B illustrate the amplitude and the transmission time for different bearing positions.
Figure 7B:
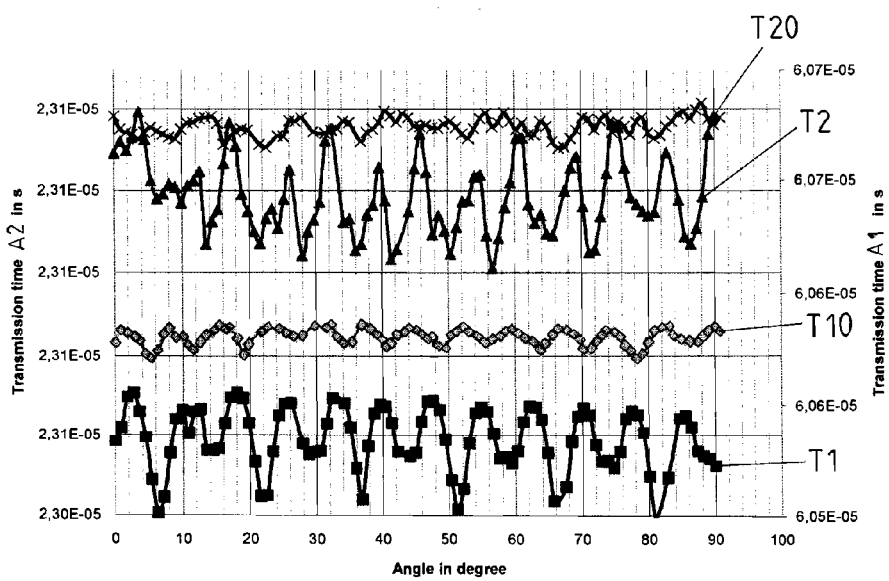

FIGS. 7A and 7B show a receiver signal (FIG. 7A: amplitude, FIG. 7B: transmission time) for a roller bearing arrangement as shown in FIGS. 5A, B in operation. Regarding FIG. 7A, the upper curves S20 and S2 correspond to the second acoustic waves A2 (shorter path) and the lower curves S10 and S1 correspond to the first acoustic waves A1 (longer path). The curves S10 and S20 are reference curves measured with a bearing without lubricant whereas the curves S1 and S2 are measured after filling in an oil lubricant.

Figure 8A:
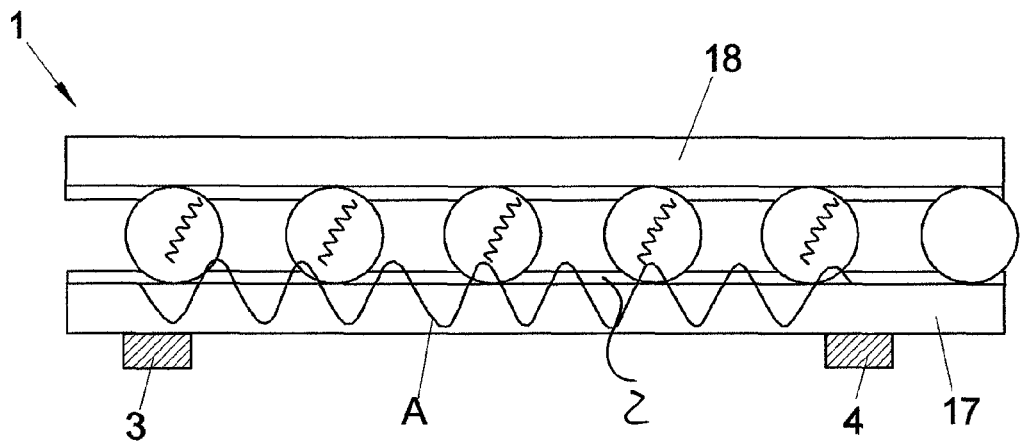
FIGS. 8A, 8B show a side view of the arrangement of FIGS. 5A and 5B in different positions.
Figure 8B:
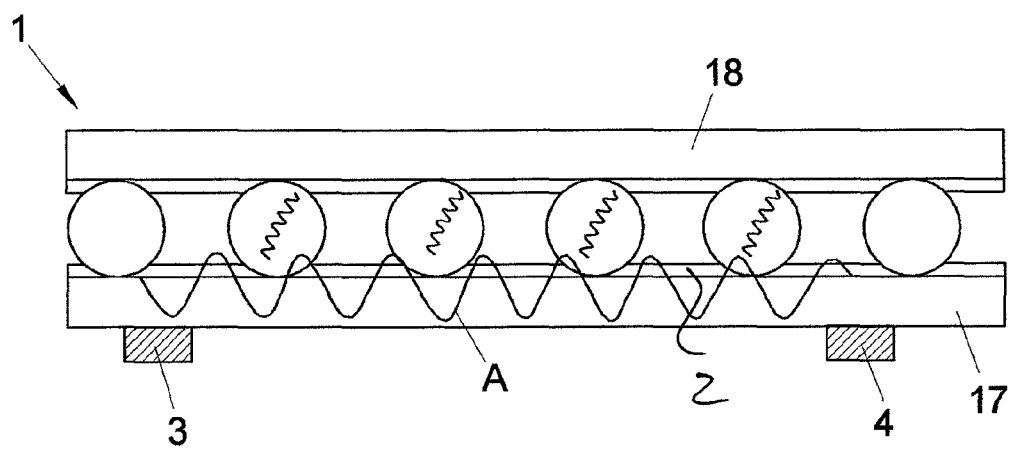

As can be seen, the amplitude of the signal varies periodically wherein the amplitude maximum gets close to the reference values. An explication for this behaviour is illustrated in FIGS. 8A and 8B, which show two different positions of the bearing. According to FIGS. 8A and 8B, the number of cylinders 16 present between the transmitter 3 and the receiver 4 will vary periodically during operation (rotation) of the bearing (FIG. 8A: five cylinders are positioned between the transmitter and the receiver, FIG. 8B: only four cylinders are present between the transmitter and the receiver). As the lubricant 2 is squeezed away by the rolling cylinders 16 (i.e. between the ring and the cylinder there is no or only a small lubricant film) the amount of lubricant that is in contact with the first bearing ring 17 will depend on the number of cylinders present between the transmitter and the receiver. This number, however, will vary periodically when the bearing is in operation.

The minimum amplitude values could be used to determine the amount of lubricant present in the bearing (in particular after a suited calibration). For example, if the difference between the reference line S10, S20 and the minimum amplitude values becomes too small an alarm signal could be triggered.

The corresponding transmission time signals T1, T10, T2, T20 (FIG. 7B), which similarly to the amplitude reflects the presence and the properties of the lubricant, shows a similar periodic dependency on the bearing position (rotation angle).

Figure 9A:
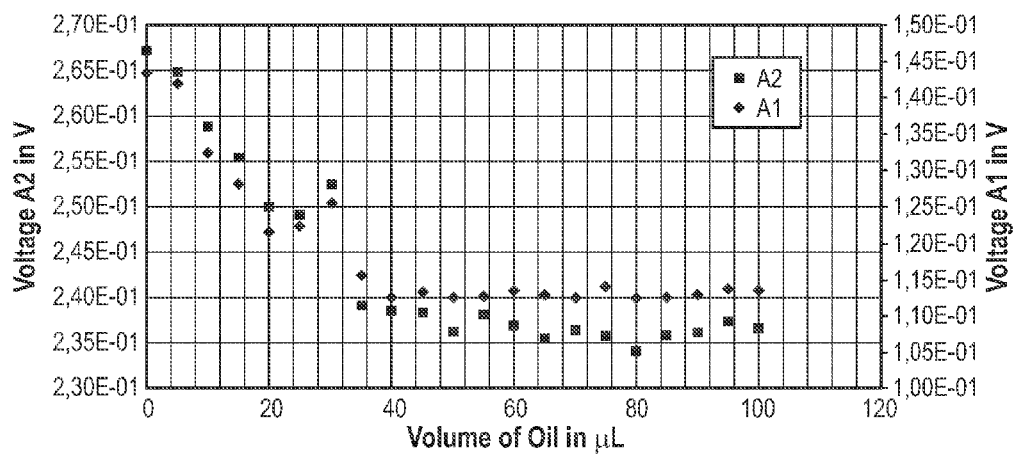
FIGS. 9A, 9B show the average amplitude and the average transmission time of a rotated bearing with respect to the lubricant volume.
Figure 9B:
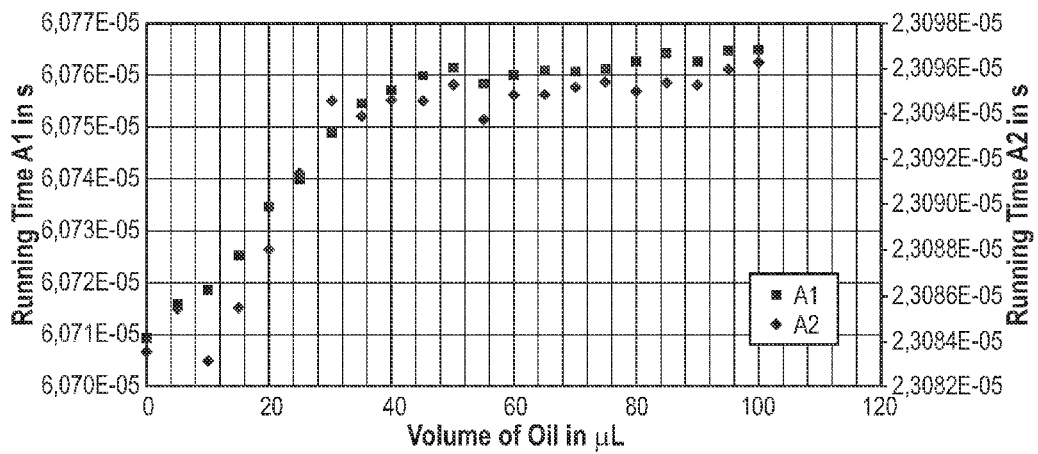

FIGS. 9A and 9B illustrate average values of the amplitude (FIG. 9A) and the transmission time (FIG. 9B) for the operated bearing (360 revolutions per minute) with respect to different volumes of the lubricant (oil).

Figure 10A:
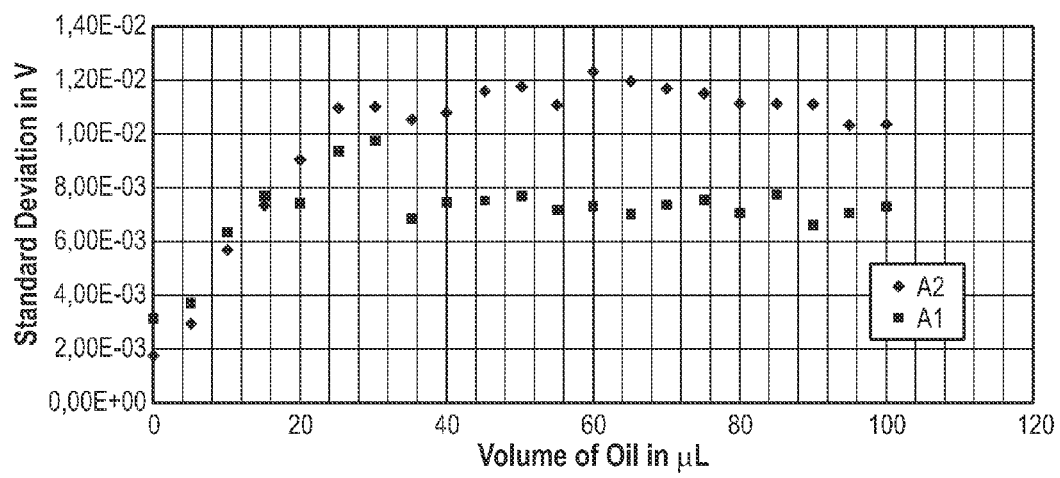
FIGS. 10A, 10B show the standard deviation of the amplitude and of the average transmission time of the rotated bearing with respect to the lubricant volume.
Figure 10B:
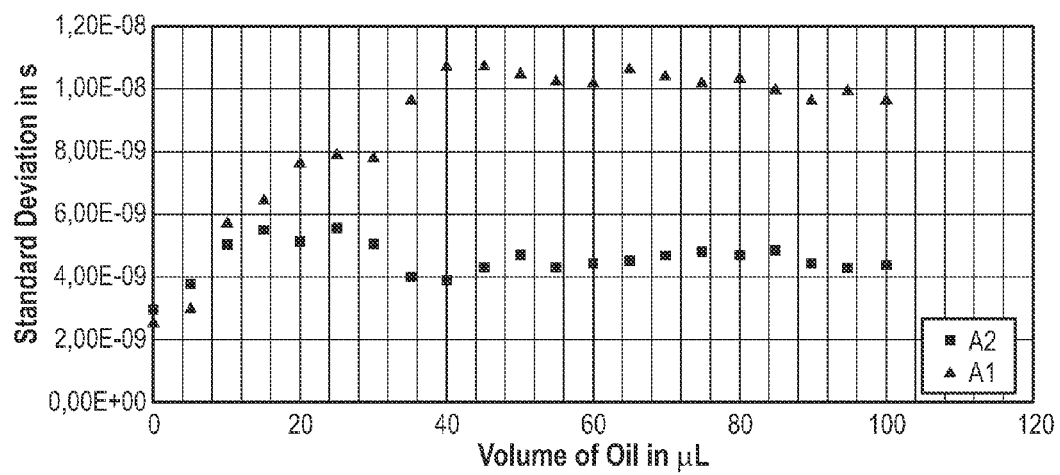

As can be clearly seen both the amplitude and the transmission time (illustrated for the waves A1 in clockwise direction and for the waves A2 in anti-clockwise direction) dependent on the amount of oil present in the bearing. Thus, it is possible—even in the operated state of the bearing—to determine the volume of lubricant in the bearing using the amplitude and/or the transmission time (of the acoustic waves), i.e. the amplitude and the time behaviour of the receiver signal. FIGS. 10A and 10B show that also the standard deviation of the amplitude (FIG. 10A) and of the transmission time (FIG. 10B) depend on the volume of lubricant present in the bearing.

The invention claimed is:

1. A bearing, comprising:
   a first and a second bearing element that are movable relative to one another;
   lubricant arranged between the first and the second bearing element for reducing the friction between the first and the second bearing element;
   at least one transmitter configured to excite concurrent surface acoustic waves in the form of Lamb waves in the first or the second bearing element, the transmitter being arranged directly on the first or the second bearing element;
   at least one receiver for receiving acoustic waves evoked by the transmitter, the receiver being arranged on the first or the second bearing element, wherein information related to properties of the lubricant can be determined using a signal generated by the receiver upon receipt of acoustic waves evoked by the transmitter.

2. The bearing as claimed in claim 1, wherein the at least one transmitter is configured to excite concurrent surface acoustic waves in the form of Lamb-Rayleigh waves in the first or the second bearing element.

3. The bearing as claimed in claim 1, wherein both the receiver and the transmitter are arranged at the first or at the second bearing element.

4. The bearing as claimed in claim 1, wherein the bearing is a rolling element bearing such that at least one rolling element is arranged between the first and the second bearing element.

5. The bearing as claimed in claim 4, wherein both the transmitter and the receiver are arranged on a side of the first or the second element that faces away from the rolling element.

6. The bearing as claimed in claim 1, wherein the bearing rolling element bearing is an axial bearing, the first bearing element forming an outer ring and the second bearing element forming an inner ring of the bearing.

7. The bearing as claimed in claim 6, wherein the transmitter and the receiver are arranged on an outer surface of the outer ring.

8. The bearing as claimed in claim 7, wherein the transmitter is arranged and configured in such a way that first acoustic waves are excited to travel along the outer ring in clockwise direction and second acoustic waves are excited to travel along the outer ring in anti-clockwise direction.

9. The bearing as claimed in claim 8, wherein the transmitter and the receiver are arranged and configured in such a way that the path length between the transmitter and the receiver in the clockwise direction is different from the path length between the transmitter and the receiver in the anti-clockwise direction.

10. The bearing as claimed in claim 9, further comprising evaluating means configured for determining information related to properties of the lubricant using a signal generated by the receiver upon receipt of acoustic waves evoked by the transmitter.

11. The bearing as claimed claim 10, wherein the evaluation means are configured to evaluate an amplitude value and a transmission time of the signal.

12. The bearing as claimed in claim 11, wherein the evaluation means are configured to evaluate a first signal generated by the receiver evoked by the first acoustic waves and a second signal generated by the receiver evoked by the second acoustic waves and to use a difference between the first and the second signal for determining the information related to properties of the lubricant.

13. A bearing, comprising:
    a first and a second bearing element that are movable relative to one another;
    a lubricant arranged between the first and the second bearing element for reducing the friction between the first and the second bearing element;
    means for exciting acoustic waves in the first or the second bearing element are configured to excite Lamb waves;
    means for receiving acoustic waves evoked in the first or the second bearing element, wherein information related to properties of the lubricant can be determined using a signal generated by the means for receiving acoustic upon receipt of acoustic waves, wherein
    the means for exciting the acoustic waves and the means for receiving the acoustic waves are configured in such a way that first acoustic waves travelling along a first path before being received by the receiving means and second acoustic waves travelling along a second path before being received by the receiving means, wherein the path lengths of the first and the second paths are different.

14. A method for determining properties of a lubricant in a bearing, the method comprising the steps of:
    a) providing a bearing having a first and a second bearing element that are movable relative to one another;
    b) arranging at least one transmitter at the first or the second bearing element and exciting acoustic waves in the first and/or the second bearing element by the use of a transmitter;
    c) arranging at least one receiver and receiving acoustic waves evoked by the transmitter using the receiver;
    d) determining information related to properties of the lubricant by evaluating a signal generated by the receiver upon receipt of acoustic waves evoked by the transmitter, wherein:
       the bearing is a rolling element bearing such that a periodic receiver signal is generated when the bearing is operated;
       registering the periodic receiver signal by the receiver;
       evaluating the periodic receiver signal by determining an average amplitude, an average transmission time of the signal, the standard deviation of the amplitude or the standard deviation of the transmission time or by evaluating the time behavior of the receiver signal; and
       determining the amount of lubricant present in the bearing using the determined average amplitude, the average transmission time of the signal, the standard deviation of the amplitude, the standard deviation of the transmission time or the evaluated time behavior of the receiver signal.

15. The method as claimed in claim 14, wherein a reference value of the signal amplitude is determined for the bearing without the lubricant and evaluating the signal comprises determining the difference between the reference value and the amplitude of the received signal.

16. A bearing, comprising:
    a first and a second bearing element that are movable relative to one another;
    a lubricant arranged between the first and the second bearing element for reducing the friction between the first and the second bearing element;
    at least one transmitter for exciting acoustic waves in the first or the second bearing element, the transmitter being arranged on the first or the second bearing element;

at least one receiver for receiving acoustic waves evoked by the transmitter, the receiver being arranged on the first or the second bearing element, wherein information related to properties of the lubricant can be determined using a signal generated by the receiver upon receipt of acoustic waves evoked by the transmitter, wherein the bearing is a rolling element bearing such that at least one rolling element is arranged between the first and the second bearing element and the transmitter is arranged and configured in such a way that first acoustic waves are excited to travel along the outer ring in clockwise direction and second acoustic waves are excited to travel along the outer ring in anti-clockwise direction.

17. The method as claimed in claim 16, wherein a reference value of the signal amplitude is determined for the bearing without the lubricant and evaluating the signal comprises determining the difference between the reference value and the amplitude of the received signal.

18. A bearing, comprising:
a first and a second bearing element that are movable relative to one another;
a lubricant arranged between the first and the second bearing element for reducing the friction between the first and the second bearing element;
at least one transmitter for exciting acoustic waves in the first or the second bearing element, the transmitter being arranged on the first or the second bearing element;
at least one receiver for receiving acoustic waves evoked by the transmitter, the receiver being arranged on the first or the second bearing element, wherein information related to properties of the lubricant can be determined using a signal generated by the receiver upon receipt of acoustic waves evoked by the transmitter, wherein the bearing is a rolling element bearing such that at least one rolling element is arranged between the first and the second bearing element and the transmitter is arranged and configured in such a way that first acoustic waves are excited to travel along the outer ring in clockwise direction and second acoustic waves are excited to travel along the outer ring in anti-clockwise direction.

\* \* \* \* \*